United States Patent [19]

Panster et al.

[11] 4,455,415
[45] Jun. 19, 1984

[54] POLYMERIC TERTIARY AND SECONDARY AMINES WITH A SILICA-TYPE BACKBONE, PROCESSES FOR THEIR PREPARATION, AND USE

[75] Inventors: Peter Panster, Rodenbach; Peter Kleinschmit, Hanau; Wolfgang Buder, Rodenbach, all of Fed. Rep. of Germany

[73] Assignee: Degussa Aktiengesellschaft, Frankfurt am Main, Fed. Rep. of Germany

[21] Appl. No.: 376,882

[22] Filed: May 10, 1982

[30] Foreign Application Priority Data

May 21, 1981 [DE] Fed. Rep. of Germany ....... 3120214

[51] Int. Cl.³ .............................................. C08G 77/00
[52] U.S. Cl. ...................................... 528/39; 528/30; 528/38; 556/413
[58] Field of Search .................... 556/413; 528/39, 30, 528/38

[56] References Cited

U.S. PATENT DOCUMENTS 3,203,969  8/1965  Pines et al. ............................ 528/39
3,592,833  7/1971  de Montigny et al. ............. 556/413
3,621,047 11/1971  Golitz et al. ........................... 528/38

FOREIGN PATENT DOCUMENTS 1506226  4/1978  United Kingdom .

*Primary Examiner*—Melvyn I. Marquis
*Attorney, Agent, or Firm*—Beveridge, DeGrandi & Kline

[57] ABSTRACT

Polymeric tertiary and secondary amines as described with a silica-type backbone, comprising units of the formula:

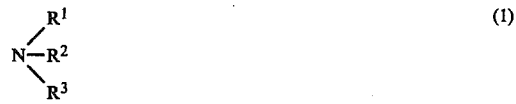

(1)

in which R¹ and R² represent a group

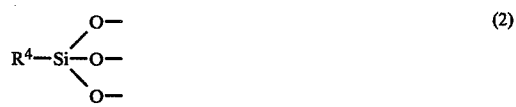
(2)

R⁴ is alkylene and the free valencies of the oxygen atoms are saturated by silicon atoms of further groups (2), if appropriate with incorporation of crosslinking agents, R³ has the same meaning as R¹ and R², or it represents hydrogen, alkyl, cycloalkyl or benzyl. Also disclosed are processes for preparing the polymeric tertiary and secondary amines and the use of these materials for removing acids from liquids and gases.

49 Claims, No Drawings

POLYMERIC TERTIARY AND SECONDARY AMINES WITH A SILICA-TYPE BACKBONE, PROCESSES FOR THEIR PREPARATION, AND USE

The invention relates to new polymeric tertiary and secondary amines with a silica-type backbone and which have a series of advantages over known organically based polymeric amines or amines fixed on a support. Processes for preparing these new products are described at the same time.

Substantially insoluble amine bases based on organic polymers have a wide field of possible uses in chemical synthesis and application. In heterogeneous reaction systems they can be used, for example for neutralizing solutions and liquids, as weakly basic ion exchange material, as adsorbents, as supports for active compounds, as supports for homogeneous catalysts which have been rendered heterogeneous or generally as a heterogeneous base in conventional organic reactions, for example in the aldol condensation reaction.

An example of one of these possible uses has been described, inter alia, in European Patent Specification 0,014,225.

However, the use of polymer bases is frequently unfavorably affected by the organic nature of the matrix whose mechanical, thermal and chemical resistance does not satisfy the demands, since organic polymers do not have a fixed structure, and their conformation and hence volume and surface area of individual particles depends strongly on external parameters such as temperature, pressure and solvent. Effective use usually also requires a swelling of the polymers in the solvent used to enable the reactants to penetrate to the amine centers. Only inorganic polymeric systems such as, for example, precipitated or pyrogenic silicas, alumina or titania, do not have these disadvantages since they have a fixed structure and the functional units are at the surface and hence more readily accessible to a possible reactant; in addition, their resistance to heat and aging is far higher than that of organic polymers. Attempts have therefore of course been made to prepare heterogeneous amine bases, for example by using aminoalkyl(alkoxy)silanes to introduce functional group into silicas. Examples of this have been described, inter alia, in British Pat. No. 1,506,226. However, inorganic polymer systems in turn have a serious disadvantage inasmuch as the number of reactive groups via which an introduction of functional groups, for example by means of aminoalkyl(alkoxy)silanes, can be effected is relatively limited so that the given amine/support ratio is unfavorably low and the presence of much interfering and surplus support material must be accepted. Furthermore, the preparation of amines thus rendered heterogeneous is elaborate, involved and expensive.

It has now been possible to find new insoluble amine bases which are distinguished by the fact that in respect of matrix properties they have the advantages of inorganic support materials but not their disadvantages, since the former have a considerably higher nitrogen content per unit weight than the latter and the functional groups are not fixed via kinetically labile Si—O—Si bonds but via more inert Si—C bonds; for it was found, surprisingly, that hydrolysis and condensation of secondary and tertiary amines at least two organic groups of which are each substituted with a trifunctional silicon atom in the form of a trialkoxysilyl grouping do not produce soluble but only completely insoluble, very inert, polymeric solids having a silica gel character. The reason this behavior is so unexpected is that a corresponding treatment of primary amines which carry a trialkoxysilyl grouping in their organic radical, such as, for example, aminopropyl(triethoxy)silane or aminoisobutyltriethoxysilane, according to German Pat. Nos. 1,023,462 and 1,158,071 does not produce insoluble but soluble polycondensates whose structural units can be described, for example in the case of the compound mentioned first by the formula $H_2N-CH_2CH_2CH_2SiO_{3/2}$.

The polymeric backbone of the compounds according to the invention, which is composed of intramolecular and intermolecular siloxane units and produced by hydrolysis and condensation of at least 2 organyltrialkoxysilyl groups present per nitrogen atom, causes the polymer bases to have physical properties similar to those of silica gels or silicas, that is to say good mechanical and thermal resistance and within wide limits independence of structure and physical state from external parameters such as pressure, temperature and solvent.

The silica-type solid formed by polycondensation has the analytical composition to be expected from the elimination of the functional groups, and its chemical behavior confirmed that this "heterogenization" does not essentially alter the structure of the amine units. The matrix of these polymeric amines can so to speak be tailored to requirements, for example as regards an aspect which is important if the polymeric amines are used as catalyst supports, namely that the amine density can be controlled by incorporating so-called crosslinking agents, for example by mixing the monomer stage with tetraalkoxysilanes, tetraalkoxy titanates or trialkoxyaluminum compounds and subsequent hydrolysis. Co-hydrolysis of the monomeric amine precursors together with tetrahalides of silicon and titanium and with the trihalides of aluminum is likewise possible but more involved and unfavorable because of the deprotonation of the polymeric amine which has to be carried out subsequently.

These new polymeric tertiary and secondary amines with a silica-type backbone thus are comprised of amine units of the general formula:

(1)

in which $R^1$ and $R^2$ represent a group of the formula:

(2)

$R^4$ denotes an alkylene group having 1 to 10 C atoms or a cycloalkylene group having 5 to 8 C atoms or represents units of the formula:

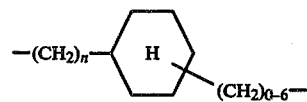

or

-continued

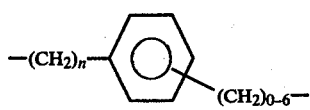

in which n indicates 1 to 6 nitrogen-terminated methylene groups, R¹ and R² can be identical or different and the free valencies of the oxygen atoms are saturated either by silicon atoms of further units of the formula (2) and/or by crosslinking bridge members:

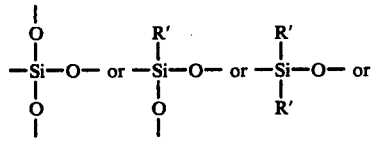

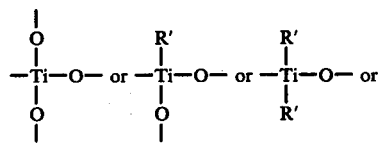

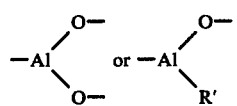

in which R' is a methyl or ethyl group and in which the ratio of the silicon atoms in (2) to the bridge atoms silicon, titanium and aluminum can be 1:0 to 1:10, R³ has the same general meaning as R¹ and R² or represents hydrogen, a linear or branched alkyl group having 1 to 10 C atoms or a cycloalkyl group having 5 to 8 C atoms or the benzyl group.

R⁴ here can be a linear or branched alkylene group, and in accordance with the preferred composition of the new polymeric bases according to the formula (1) R¹, R² and R³ each have the same meaning or are identical to one another. These polymers are preferred because they are particularly stable and resistant to chemical attacks and are also distinguished by an extremely high resistance to alkali.

Some of the monomeric precursors to these polymeric amines are known but some are new compounds. Their composition can be described by way of example by formulae such as:

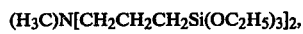

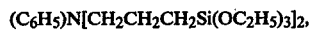

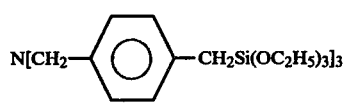

and correspondingly the composition of polymer units which can be prepared therefrom can be described by formulae such as

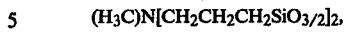

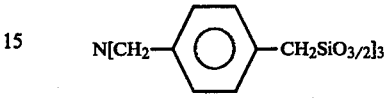

Particular benefits in respect of the availability of the starting materials and the material properties of the polymer are obtained by means of an amine composed of units of the formula:

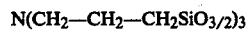

The invention also relates to a process for preparing the polymeric amines and also comprising a new way of preparing a large proportion of the monomeric precursors. U.S. Pat. No. 2,715,133 also describes a similar reaction but the process for product formation clearly differs from the process according to the invention since the reaction times chosen are markedly shorter.

The process comprises reacting a primary amine having a substituent comprising:
an alkyl group having 1 to 10 C atoms,
a cycloalkyl group having 5 to 8 C atoms,
a benzyl group,
an alkylene group having 1 to 10 C atoms or a cycloalkylene group having 5 to 8 C atoms, either group being bonded to a trialkoxysilyl group having alkoxy radicals which contain 1 to 5 C atoms,
or of a group:

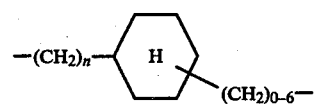

or

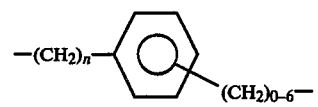

in which n indicates 1 to 6 nitrogen-terminated methylene groups,
with a halogenoorganotrialkoxysilane having alkoxy groups which contain 1 to 5 C atoms and in which the organic group is alkylene having 1 to 10 C atoms, cycloalkylene having 5 to 8 C atoms or groups

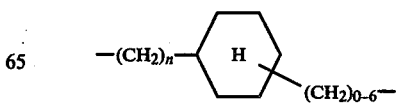

or

in which n indicates 1 to 6 halogen-terminated methylene groups, in the course of 5 to 48 hours, if appropriate in a solubilizer, deprotonating the resulting quaternary salts, if appropriate in a solubilizer, by means of at least stoichiometric amounts of an organic or inorganic base, separating the resulting inorganic salt, if appropriate, from the liquid phase, separating the latter by distillation into the amine components formed and reacting the component with predominantly contains tertiary amine, if appropriate after the addition of a solubilizer and/or of a crosslinking agent of the general formula $$Me(OR)_{2-4}R'_{0-2} \text{ or } Me(OR)_{2-3}R'_{0-1}$$

in which Me denotes Si, Ti or Al, R is an alkyl group having 1 to 5 C atoms and R' is methyl or ethyl, with at least the amount of water required for complete hydrolysis and condensation, and drying, if necessary heat-treating, milling and/or classifying the resulting solid.

The overall reaction which takes place in the process and its stoichiometry is well represented in the general empirical equation (Equation (I)) below:

$$2I-R^{1'}+2H_2N-R^{3'} \rightarrow (H-NR_2^{1'}R^{3'}-)^+I^- +(H_3NR^{3'})^+I^- \quad (I)$$

in which $R^{1'}$ represents a precursor of the groups $R^1$ and $R^2$ where the functional alkoxy groups are still present at the Si atom and $R^{3'}$ likewise represents the functional precursor of $R^3$ or it can also have the same meaning as $R^3$, namely when $R^3$ represents a linear or branched alkylene group containing 1 to 10 C atoms, a cycloalkylene group containing 5 to 8 C atoms or the benzyl group.

After this first stage has been carried out, the second step, for which the product mixture can remain in the reactor originally used, brings the deprotonation of the two quaternary salts by reaction with stoichiometric or excess amounts of a base, such as an alkali metal hydroxide, alkaline earth metal hydroxide or ammonia, but preferably an alkali metal methylate, ethylate, n- or i-propylate, n- or i-butylate or n-pentylate, with or without use of a solubilizer of the above-mentioned type, in accordance with general Equation (II) below, in which the base used is abbreviated to $B^-$ and otherwise $R^{1'}$ and $R^{3'}$ have the scope of meaning as in Equation (I).

$$(H-NR_2^{1'}R^{3'})^+I^- +(H_3NR^{3'})^+I^- +2B^- \rightarrow NR_2^{1'}R^{3'}+H_2NR^{3'}+2BH+2I^- \quad (II)$$

A solubilizer which can be used in the reaction according to Equation (II) and which advisedly is identical to the solubilizer used in the reaction according to Equation (I), if used at all, in principle is any organic liquid which in a mixture with the oily quaternary salts is capable of at least partially dissolving the base; however, here also it is preferable to use alcohols corresponding to the alkoxy groupings on the Si, such as methanol, ethanol, n- or i-propanol, n- or i-butanol or n-pentanol.

This second process stage is initially followed by the separation of the inorganic salt formed in the deprotonation from the reaction mixture by means of conventional techniques such as filtration, centrifuging and/or decanting, together with a single or repeated washing, by means of a solubilizer of the type mentioned, of the solids separated off. The product mixture combined with the washings is then freed by distillation in the sequence of the boiling points from solubilizer and primary amine by-product $H_2NR^{3'}$ present, if appropriate with the use of a vacuum.

While the primary amine, possibly after purification, can be returned into the process according to Equation (I) the quantitatively formed tertiary amine is converted by hydrolysis and condensation into the polymeric amine according to the invention of the general formula (I). For this purpose, a stoichiometric, relative to complete hydrolysis and condensation, but preferably excess amount of water is added to the tertiary amine with or without the use of a solubilizer, preferably with the use of 1 to 1,000% by weight of the alcohol which corresponds to the particular alkoxy groupings on the silicon atoms, such as methanol, ethanol, n- or i-propanol, n- or i-butanol or n-pentanol, with stirring and at room temperature or at an elevated temperature up to the reflux temperature of the solubilizer/amine mixture (under atmospheric pressure). The mixture normally already solidifies on addition of a part of the water and turns into a pudding-type material which, if appropriate after addition of a further amount of solubilizer, is converted by means of vigorous stirring below the reflux temperature into a highly dispersed suspension.

If no spontaneous polycondensation takes place, it is advantageous in some cases to add to the still homogeneous solution a condensation catalyst, for example in the form of catalytic amounts of acid or a small amount of polymeric product already present. The solid can be separated from the suspension thus formed by means of conventional techniques, namely by filtration, centrifuging and/or decanting, or the volatile constituents of the product suspension can also be removed from the solid by distillation, if appropriate using a vacuum.

The isolated product is then dried at temperatures of room temperature to 250° C., possibly with the use of a vacuum. After all adhering residues of the water/solubilizer mixture and of the eliminated alcohol have been removed, drying can be followed by a heat treatment of the product at about 200°–350° C. which in turn, if appropriate, can be carried out with the use of a vacuum. The dry product is either used directly or, to increase the particle fineness and the surface area, it is additionally milled and classified. However, it is also possible to mill the product at the precipitation suspension stage.

When incorporating so-called crosslinking agents by co-precipitating the monomeric base together with, for example, tetraalcoholates or tetrahalides of silicon or titanium or aluminum trialcoholates or trihalides, it is advantageous to combine base and crosslinking agent only shortly before the hydrolysis and condensation since otherwise the preparation process according to Equations (I) and (II) can be disrupted. When using tetrahalides of silicon or titanium or trihalides of aluminum, the heterogenization must be followed by a deprotonation of the resulting ammonium salts by reaction with an alkali metal hydroxide, alkaline earth metal hydroxide, sodium bicarbonate, ammonia, or primary, secondary or tertiary amines and subsequent thorough washing-out or extracting of the separated-off solid with water.

The new inorganic polymer systems can be characterized in particular by means of the hydrolysis yield, elemental analyses and by determination of their basicity. Depending on the pretreatment, the polymeric bases have specific surface areas of 0.1 to 3,000 m²/g and particle size diameters from about 1 cm to 1 μm. In air they are stable up to at least 200° C., in some cases even to over 275° C. Under a protective gas atmosphere they are thermally stable to over 400° C.

In addition to the preparation method described and discussed above for obtaining tertiary polymeric amines, other process variants are also possible and to which the invention also relates but which use secondary amines instead of primary amines as starting materials.

One of these process variants comprises reacting a secondary bis-(trialkoxysilylorgano)-amine in which the organic group has the meaning of $R^4$ and the alkoxy groups have 1 to 5 C atoms with a halogenoorganotrialkoxysilane in which organic group and alkoxy groups have the same meaning as in the case of the amine reactant, or with a linear or branched alkyl halide having 1 to 10 C atoms, a cycloalkyl halide having 5 to 8 C atoms or a benzyl halide, deprotonating the resulting quaternary salt, if appropriate in a solubilizer, with at least stoichiometric amounts of an organic or inorganic base, separating the resulting inorganic salt, if appropriate, from the liquid phase and further processing the tertiary amine in a manner corresponding to that which has already been described at above and which uses primary amines as starting materials. In this process also the component which predominantly contains tertiary amine, if appropriate after the addition of a solubilizer and/or a crosslinking agent, is completely hydrolyzed and condensed, and the solid then dried and, if appropriate, heat-treated, milled and/or classified.

Another process variant also uses a secondary amine as a starting material and proposes reacting a secondary amine having a trialkoxysilylorgano substituent in which the organic group has the same meaning of $R^4$ and the alkoxy groups have 1 to 5 C atoms and a substituent comprised of a linear or branched alkyl group having 1 to 10 C atoms or a cycloalkyl group having 5 to 8 C atoms or a benzyl group with a halogenoorganotrialkoxysilane in which organic group and alkoxy groups have the same meaning as in the case of the trialkoxysilylorgano substituents of the amine reactant, deprotonating the resulting quaternary salt, if appropriate in a solubilizer, with at least stoichiometric amounts of an organic or inorganic base, separating the resulting inorganic salt, if appropriate, from the liquid phase and further processing the tertiary amine in a manner which corresponds to the procedure of the process variant described above.

In all the process variants hitherto disclosed, advantageous individual measures can be applied in the same way. These measures include the choice of halogen in the halogenoorgano compounds used, the structure of the alkyl radical and/or trialkoxysilylalkyl radical on the amine nitrogen and of the alkyl radical in the halogenoalkyltrialkoxysilane, and also include the reaction conditions for the reaction between amine and halogen compound, the selection of a particularly suitable deprotonating agent and suitable solvents for the deprotonation and finally the conditions for hydrolysis and polycondensation as well as for the working-up of the polycondensate.

It has thus been found that primary and secondary amines can be reacted with iodo-, bromo- or chloroorganotrialkoxysilanes.

It has also been found that there are no evident changes in the course of the individual reaction stages if the alkyl radical and/or trialkoxysilylalkyl radical on the amine nitrogen and the alkyl radical in the halogenoalkyltrialkoxysilane are linear or branched.

The reaction of the amine with the halogenoorganotrialkoxysilane is preferably carried out at a temperature between room temperature and 300° C.

The reaction can also be carried out under an elevated pressure which corresponds to the sum of the partial pressures of the components of the reaction mixture at the reaction temperature used.

It has also been found that the deprotonation can be very readily carried out by means of sodium methylate, potassium methylate, sodium ethylate, potassium ethylate, sodium propylate, potassium propylate, sodium butylate, potassium butylate, sodium pentylate or potassium pentylate, but also still readily by means of less expensive agents, such as alkali metal hydroxide, alkaline earth metal hydroxide, alkali metal bicarbonate, alkali metal carbonate or ammonia.

Furthermore, the way the process is carried out is very much simplified when the deprotonation is carried out in an organic solvent, in particular in an alcohol which corresponds to the alkoxy radicals bonded to the silicon atoms of one or both reactants.

It was also possible to determine that the hydrolysis and condensation can be carried out at room temperature to reflux temperature of the reaction mixture, so that up to this upper limit it is possible to utilize an increase in temperature to increase the rate of the reaction.

To dry the polycondensate, a step which can also be carried out in vacuo, temperatures from room temperature to 250° C. can be used.

Finally, a heat treatment, depending on use, may benefit the utilizability of the process products.

In one advantageous embodiment of this after-treatment stage, a heat treatment, if appropriate in vacuo, is carried out for at least one hour up to four days at 200°–350° C.

Finally it has been found that the secondary polymeric amines can be prepared in a very simple manner from monomers which can be obtained by processes which are in themselves known. A corresponding development of the invention proposes a way of carrying out the process which deviates from the process variants hitherto discussed and which comprises reacting a bis-(trialkoxysilylorgano)-amine in which the organic group has the meaning of $R^4$ and the alkoxy groups have 1 to 5 C atoms, if appropriate after the addition of a solubilizer, with at least the amount of water required for complete hydrolysis and condensation and further processing the resulting solid in a manner corresponding to that described above.

In this process also, whether the trialkoxysilyl radicals on the amine nitrogen are linear or branched makes no essential difference.

The hydrolysis and condensation can also be carried out at room temperature to reflux temperature of the reaction mixture.

The drying of the polycondensate can likewise be carried out at room temperature to 250° C. and, if desired, in vacuo.

Finally, as regards a heat treatment of the dried polycondensate the same points apply as made for the case of polycondensate obtainable by the preparation ways discussed in detail above.

A particularly useful process which proposes ammonia, which is very inexpensive, as a nitrogen-containing starting material could finally be realized for preparing the tertiary polymeric amines. The process proposes reacting ammonia with a halogenoorganotrialkoxysilane in which the organic group has the meaning of $R^4$ and the alkoxy groups have 1 to 5 C atoms, if appropriate in the presence of a solubilizer, at temperatures from below room temperature to 250° C. and under a pressure which corresponds to the sum of the partial pressures of the components of the reaction mixture at the reaction temperature used, 1-20 moles of ammonia being employed per 1 mole of halogenoorganosilane, initially substantially removing excess ammonia, separating off the resulting inorganic salt, removing by distillation ammonia residues as well as small amounts of primary and secondary amines which have been formed and, if used, solubilizer and further processing the remaining tertiary amine in a manner which is in accordance with the measures of the other process variants discussed above.

It is also true for this process that the halogenoorganotrialkoxysilane with which the ammonia is reacted can be an iodine compound, bromine compound or chlorine compound and that the alkyl radical in the halogenoalkyltrialkoxysilane can be linear or branched.

The new polymeric tertiary and secondary amines with a silica-type backbone can in principle be used in the same areas of application as mentioned at the outset by way of example for substantially insoluble amine bases based on organic polymers, but they are not limited to these. A characteristic use of the polymeric tertiary and secondary amines which are characterized by their weakly basic character and which use is also a subject of the invention comprises the removal of acids from liquids and gases.

The invention is illustrated in more detail by means of the illustrative examples below.

EXAMPLE 1

2,093.20 g (6.3 moles) of $I-CH_2CH_2CH_2Si(OC_2H_5)_3$ were added in the course of 1 hour at approximately room temperature to a solution of 218.73 g (7.04 moles) of $CH_3NH_2$ in 1,700 ml of ethanol, and the resulting mixture was then heated under reflux for 20 hours. The reaction mixture was then cooled down to 50° C., a solution of 574.89 g (8.45 moles) of $NaOC_2H_5$ in 3 liters of ethanol was added in the course of 1 hour, and the resulting mixture was stirred for a further 2 hours under reflux. After the alcohol present and excess methylamine had been removed by distillation in a rotary evaporator, 1.5 liters of diethyl ether were added, and the sparingly soluble salts were filtered off with suction and washed with 250 ml of diethyl ether, and the diethyl ether in turn was removed by distillation. The remaining liquid was initially separated from a small amount of a second phase which was present in the form of a viscous oil at the bottom of the vessel and then subjected to fractional distillation. The desired product $H_3CN[CH_2CH_2CH_2Si(OC_2H_5)_3]_2$ distilled over under a pressure of 0.8 mbar at a temperature of 150°-152° C.

The yield, calculated according to Equations (I) and (II) in the description section, was 983.48 g and thus 71% of theory. The product was dissolved in 1 liter of ethanol, and 1 liter of demineralized water was added with gentle stirring in the course of 15 minutes at 50°-55° C. to the solution. The mixture was then heated up to reflux temperature and the contents instantaneously solidified into a pudding-like material which, in the course of a further 3 hours of stirring, was dispersed to give a highly dispersed suspension.

The solids were then filtered off and washed several times with a total of 5 liters of water, and the product was dried for 12 hours at 150° C./100 mbar and milled in a pin mill.

Complete hydrolysis and condensation of the monomer product used would produce 486.15 g of polymeric product; 485.2 g were obtained, this corresponds to 99.8% of theory. The analytical data determined likewise confirmed the composition of the polymer units of the formula $H_3CN[CH_2CH_2CH_2SiO_{3/2}]_2$.

|         | % of C | % of H | % of N |
|---------|--------|--------|--------|
| Theory: | 38.68  | 6.96   | 6.44   |
| Found:  | 37.93  | 6.96   | 6.97   |

An investigation by means of differential scanning colorimetry (DSC) showed the start of an exothermic decomposition at 222° C. in air and the start of an endothermic decomposition at 390° C. under a nitrogen atmosphere. The specific surface area of the product, determined in an Areameter, was 1.8 $m^2/g$.

EXAMPLE 2

493.58 g (2.32 moles) of chloromethyltriethoxysilane were added in the course of 2 hours with stirring at 50° C. to 300 g (2.32 moles) of octylamine. The mixture was then stirred for 30 hours at 180° C. and then cooled down to room temperature, and 157.88 g (2.32 moles) of $NaOC_2H_5$, dissolved in 1 liter of ethanol, were added in the course of 30 minutes. The resulting mixture was stirred for a further 2 hours at reflux temperature, and the alcohol present was then distilled off, and the solids were filtered off and washed with n-hexane, and the n-hexane in turn was removed by distillation.

The remaining liquid was charged into a thin-film evaporator in which, at a heating jacket temperature of 120° C. and under a vacuum of 0.8 mbar, the octylamine liberated in the deprotonation and small amounts of other readily volatile contaminants were removed overhead. The resulting bottom product was directly mixed with 0.6 liter of toluene, the resulting mixture was heated to 60° C., and 500 ml of water were added with stirring in the course of 20 minutes. Stirring was continued for a further 1 hour at the same temperature, during which period a yellowish-white precipitate was formed. This was then stirred for a further 4 hours at the reflux temperature, then filtered off and washed first with ethanol and then with much water and finally dried for 24 hours at 120° C./100 mbar. 306.99 g (102.0% of theory) of a polymeric product composed of units of the formula $C_8H_{17}N[CH_2SiO_{3/2}]_2$ were obtained.

| Analytical data: | % of C | % of H | % of N |
|------------------|--------|--------|--------|
| Theory:          | 46.29  | 8.16   | 5.40   |
| Found:           | 45.43  | 8.21   | 5.82   |

EXAMPLE 3

391.2 g (104.6% of theory) of a polymeric amine, essentially comprised of polymer units of the formula $C_6H_{11}N[CH_2CH_2CH_2SiO_{3/2}]_2$ which can also be supported by the following comparison of the various theoretical and found analytical data were obtained from 260.0 g (2.62 moles) of cyclohexylamine and 857.6 g (2.62 moles) of bromopropyltriisopropoxysilane in a manner analogous to Example 2.

|  | % of C | % of H | % of N |
|---|---|---|---|
| Theory: | 50.59 | 8.12 | 4.91 |
| Found: | 49.98 | 8.23 | 5.37 |

EXAMPLE 4

318.1 g (97.2% of theory) of a polymeric amine comprised of units of the formula

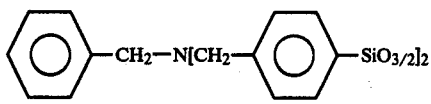

were obtained from 180 g (1.68 moles) of benzylamine and 485.3 g (1.68 moles) of

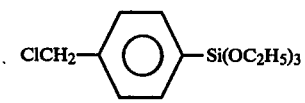

in a manner analogous to Example 2. The analytical data were as follows:

|  | % of C | % of H | % of N | % of Si |
|---|---|---|---|---|
| Theory: | 64.75 | 4.92 | 3.60 | 14.42 |
| Found: | 65.73 | 5.62 | 3.99 | 13.71 |

After milling and heat treatment for 3 days at 250° C./1 mbar the product had a specific surface area, determined on an Areameter, of 423 m²/g.

EXAMPLE 5

1,490.4 g (7.5 moles) of $Cl—CH_2CH_2CH_2Si(OCH_3)_3$ were added dropwise in the course of 2 hours at room temperature to 1,344.6 g (7.5 moles) of $H_2N—CH_2CH_2CH_2Si(OCH_3)_3$. The mixture was then heated up to 150° C., stirred for 15 hours at this temperature and thereafter cooled down to room temperature, and first 1 liter of dried methanol and then a total of 405.2 g (7.5 moles) of $NaOCH_3$, in portions, were added, during which addition the temperature increased to 60° C. After a further 3 hours' stirring under reflux, the resulting sodium chloride was filtered off and washed out with a total of 1 liter of methanol. After the washings had been combined with the product mixture, the methanol was removed by distillation at a bottom temperature of 60°–80° C. and under a pressure of 50 mbar, and the remaining liquid was charged into a Sambay evaporator. At a heating jacket temperature of 130° C. and under a vacuum of 0.4 mbar, it was possible to obtain 611.8 g (91.0% of theory) of $H_2N—CH_2CH_2CH_2Si(OCH_3)_3$ as top product.

2 liters of methanol were added to the bottom product which essentially comprises the tertiary base $N[CH_2CH_2CH_2Si(OCH_3)_3]_3$, and the resulting mixture was heated up with stirring to 50° C. 3 liters of water were then added in the course of 30 minutes. Already on addition of a part of the water spontaneous polycondensation of the amine commenced. The reaction mixture was heated up with slow stirring to the reflux temperature and refluxed for 2 hours, and the suspension was then treated for 10 minutes by means of an Ultra-Turrax disperser. After the finely divided solid had been separated from the liquid phase by centrifuging, it was initially dried for 12 hours at 180° C. and then heat-treated for 12 hours at 250° C./100 mbar. It was possible to obtain 1,160.0 g (104.3% of theory) of a polymeric amine comprised of structural units of the formula $N[CH_2CH_2CH_2SiO_{3/2}]_3$.

| Analytical data: | % of C | % of H | % of N | % of Si |
|---|---|---|---|---|
| Theory: | 36.46 | 6.12 | 4.72 | 28.42 |
| Found: | 35.61 | 5.99 | 5.12 | 27.29 |

The specific surface area of the product, determined on an Areameter, was 315 m²/g. A DSC investigation showed decomposition commencing at 290° C. in air and at 408° C. in a nitrogen atmosphere.

EXAMPLE 6

138.6 g (96.9% of theory) of a polymeric amine comprised of units of the formula $N(CH_2SiO_{3/2})[(CH_2)_8SiO_{3/2}]_2$ were obtained from 195.0 g (0.70 mole) of $H_2N—CH_2Si(OC_4H_9)_3$ and 252.2 g (0.70 mole) of $I—(CH_2)_8Si(OCH_3)_3$ in a manner analogous to Example 5.

| Analytical data: | % of C | % of H | % of N | % of Si |
|---|---|---|---|---|
| Theory: | 49.96 | 8.39 | 3.43 | 20.62 |
| Found: | 48.99 | 8.22 | 3.76 | 21.20 |

EXAMPLE 7

176.3 g (102.1% of theory) of a polymeric amine comprised of units of the formula:

were obtained from 240.6 g (1.02 moles) of

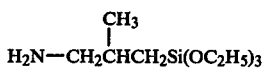

and 259.9 g (1.02 moles) of

in a manner analogous to Example 5.

| Analytical data: | % of C | % of H | % of N | % of Si |
|---|---|---|---|---|
| Theory: | 42.57 | 7.15 | 4.14 | 24.89 |

-continued

| Analytical data: | % of C | % of H | % of N | % of Si |
|---|---|---|---|---|
| Found: | 41.73 | 7.46 | 4.81 | 24.90 |

EXAMPLE 8

1,344.06 g (7.5 moles) of $H_2N-CH_2CH_2CH_2Si(OCH_3)_3$ and 1,490.4 g (7.5 moles) of $Cl-CH_2CH_2CH_2Si(OCH_3)_3$ were reacted in a manner analogous to Example 5. However, an equimolar amount (3.75 moles) of $Si(OCH_3)_4$ was added before the hydrolysis to the initially resulting tertiary base $N[CH_2CH_2CH_2Si(OCH_3)_3]_3$. After the further procedure followed was as in Example 5, 1,339.9 g (100.2% of theory) of a crosslinked polymeric amine comprised of structural units of the formula $N[CH_2CH_2CH_2SiO_{3/2}]_3 \cdot SiO_2$ were obtained.

| Analytical data: | % of C | % of H | % of N | % of Si |
|---|---|---|---|---|
| Theory: | 30.31 | 5.09 | 3.93 | 31.51 |
| Found: | 28.97 | 5.35 | 4.38 | 30.62 |

According to a DSC investigation, the polymeric product decomposed exothermically at a temperature of 275° C. in air and endothermically at a temperature of 429° C. under a nitrogen atmosphere. The result of a surface area determination was a specific surface area of 215 m²/g.

EXAMPLE 9

1,137.5 g (95.1% of theory) of a polymeric product comprised of polymer units of the formula $N[CH_2CH_2CH_2SiO_{3/2}]_3 \cdot (C_2H_5)_2SiO$ were obtained from 1,075.7 g (6.0 moles) of $H_2N-CH_2CH_2CH_2Si(OCH_3)_3$, 1,192.3 g (6.0 moles) of $Cl-CH_2CH_2CH_2Si(OCH_3)_3$ and 444.8 g (3.0 moles) of $(C_2H_5)_2Si(OCH_3)_2$ in a manner analogous to Example 8.

| Analytical data: | % of C | % of H | % of N | % of Si |
|---|---|---|---|---|
| Theory: | 39.16 | 7.08 | 3.51 | 28.18 |
| Found: | 39.01 | 7.38 | 3.90 | 27.29 |

EXAMPLE 10

310.3 g (1.07 moles) of $I-CH_2CH_2CH_2Si(OCH_3)_3$ were dissolved in 100 ml of dried methanol. 365.5 g (1.07 moles) of $HN[CH_2CH_2CH_2Si(OCH_3)_3]_2$ were added dropwise in the course of 2.5 hours with stirring to this solution which had been heated up to the reflux temperature. After the addition was complete, stirring was carried out for a further hour under reflux. 63.7 g (1.18 moles) of $NaOCH_3$ were then added in portions to the solution which had cooled down to room temperature, stirring was carried out for a further 2 hours under reflux, and the resulting NaI was centrifuged off at room temperature. 500 ml of water were added dropwise at room temperature with slow stirring directly to the centrifugate. During the addition, the contents of the flask solidified into a gel-type material which, in the course of a further 2.5 hours of stirring under reflux, was converted into a finely dispersed suspension. After filtration and 12 hours' drying at 150° C./100 mbar, 314.7 g (99.2% of theory) of a polymeric product comprised of polymer units of the formula $N[CH_2CH_2CH_2SiO_{3/2}]_3$ were obtained.

| Analytical data: | % of C | % of H | % of N | % of Si |
|---|---|---|---|---|
| Theory: | 36.46 | 6.12 | 4.72 | 28.42 |
| Found: | 35.10 | 6.07 | 4.89 | 27.17 |

EXAMPLE 11

250.0 g (0.86 mole) of $I-CH_2CH_2CH_2Si(OCH_3)_3$ and 294.3 g (0.86 mole) of $HN[CH_2CH_2CH_2Si(OCH_3)_3]_2$ were reacted in a manner analogous to Example 10. Before the addition of the water, 139.5 g (0.86 mole) of $Al(OC_2H_5)_3$ were added to the product solution. After further treatment as in Example 10, a polymeric product comprised of units of the approximate formula $N[CH_2CH_2CH_2SiO_{3/2}]_3 \cdot AlO_{3/2}$ was obtained. Yield: 304.2 g (101.8% of theory).

| Analytical Data: | % of C | % of H | % of N | % of Si | % of Al |
|---|---|---|---|---|---|
| Theory: | 31.11 | 5.22 | 4.03 | 24.25 | 7.76 |
| Found: | 30.22 | 5.07 | 4.46 | 23.86 | 6.79 |

EXAMPLE 12

190.6 g (0.42 mole) of

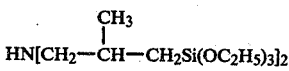

were added with vigorous stirring in the course of 2 hours to 81.1 g (0.42 mole) of hot 2-bromooctane at 100° C. The mixture was then stirred for a further 3 hours at this temperature and then cooled down to room temperature, and a solution of 23.6 g (0.42 mole) of KOH in 200 ml of methanol was added in the course of 1 hour. After the resulting mixture had been stirred for a further hour at 60° C., 200 ml of water were added in the course of 15 minutes at this temperature. Further stirring was carried out for 1 hour at 60° C. and then for 3 hours under reflux. The precipitated form was filtered off, washed first with methanol and then with water, and thereafter dried at 120° C./100 mbar for 24 hours. After milling in a pin mill, it was possible to obtain 138.7 g (96.1% of theory) of a polymeric amine comprised of units of the formula:

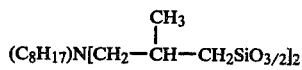

| Analytical data: | % of C | % of H | % of N | % of Si |
|---|---|---|---|---|
| Theory: | 55.93 | 9.68 | 4.08 | 16.35 |
| Found: | 54.86 | 9.18 | 4.36 | 15.87 |

EXAMPLE 13

101.6 g (98.9% of theory) of a polymeric amine having units of the formula

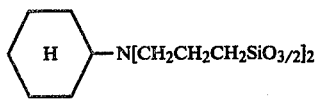

were obtained from 124.4 g (0.36 mole) of

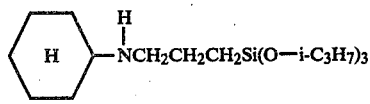

and 117.8 g (0.36 mole) of initially introduced Br—$CH_2CH_2CH_2Si(O—i—C_3H_7)_3$ in a manner analogous to Example 12.

| Analytical data: | % of C | % of H | % of N | % of Si |
|---|---|---|---|---|
| Theory: | 50.49 | 8.12 | 4.91 | 19.68 |
| Found: | 49.37 | 7.90 | 5.23 | 18.76 |

EXAMPLE 14

160.2 g (0.68 mole) of $(H_3C)NH—CH_2CH_2CH_2Si(OC_2H_5)_3$ and 194.0 g (0.68 mole) of initially introduced Br—$CH_2CH_2CH_2Si(OC_2H_5)_3$ were first reacted in accordance with Example 12. Deprotonation was then effected by means of the addition of 65.4 g (0.68 mole) of Na—n—$OC_4H_9$, dissolved in 400 ml of n—$C_4H_9OH$, in the course of 30 minutes. The resulting mixture was stirred for a further 2 hours at 100° C., and 44.2 g (0.17 mole) of $Ti(OC_2H_5)_4$ and then 200 ml of water were added to the cooled-down solution at 50° C. Stirring was carried out for a further 3 hours at 100° C., and thereafter the resulting polymer, comprised of units of the formula:

$(H_3C)N[CH_2CH_2CH_2SiO_{3/2}]_2.0.25TiO_2$ was further treated in a manner analogous to Example 12. Yield: 156.7 g (97.1% of theory).

| Analytical data: | % of C | % of H | % of N | % of Si | % of Ti |
|---|---|---|---|---|---|
| Theory: | 35.42 | 6.37 | 5.90 | 23.67 | 5.05 |
| Found: | 34.47 | 6.42 | 6.01 | 22.80 | 4.87 |

EXAMPLE 15

200.0 g (0.44 mole) of

were dissolved in 200 ml of $C_2H_5OH$. 200 ml of demineralized water were added dropwise in the course of 30 minutes to this solution which had been warmed to 50° C. The suspension of the instantaneously formed solid was stirred for a further 25 hours under reflux, and the further procedure followed was as in Example 5. 105.0 g (103.1% of theory) of a polymeric product having units of the formula:

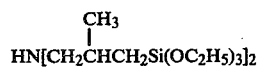

were obtained.

| Analytical data: | % of C | % of H | % of N | % of Si |
|---|---|---|---|---|
| Theory: | 41.52 | 7.41 | 6.05 | 24.27 |
| Found: | 40.37 | 7.28 | 5.95 | 26.41 |

EXAMPLE 16

2,406 g (10.0 moles) of Cl—$CH_2CH_2CH_2Si(OC_2H_5)_3$ 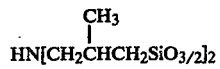 and 567.2 g (33.3 moles) of liquid $NH_3$ were combined in a 5 l lift autoclave. The mixture was heated up to 150° C. and then an initial pressure of about 65 bar became established. After 24 hours' stirring, a final pressure of about 50 bar established itself. The autoclave was cooled down and the pressure was released at room temperature and a large part of the excess $NH_3$ vaporized. The ammonium chloride formed was filtered off and washed out with a total of 500 ml of methylene chloride. After the washings and filtrate had been combined, first the methylene chloride was removed in a rotary evaporator. The remaining bottom product was charged into a thin-film evaporator where, at a jacket temperature of 150° C. and under a pressure of 0.6 mbar, readily volatile constituents, including also $H_2N—CH_2CH_2CH_2Si(OCH_3)_3$, were removed. 1,526 g of $N[CH_2CH_2CH_2Si(OC_2H_5)_3]_3$, which corresponds to a 72.7% conversion into the desired product of the $ClCH_2CH_2CH_2Si(OC_2H_5)_3$ used, remained as sparingly volatile fraction, to which 1,500 ml of ethanol were then added, and the mixture was heated up to 70° C. 1 liter of water was then added in the course of 1 hour with slow stirring. Stirring was carried out for a further 1 hour at this temperature and then for 3 hours under reflux. The resulting solids were filtered off, washed with 1 liter of water, dried for 24 hours at 150° C./100 mbar, heat-treated for 12 hours at 260° C. and then milled and classified into different particle sizes. A total of 705.9 g (98.3% of theory, relative to monomeric product) of a polymeric base comprised of units of the formula $N[CH_2CH_2CH_2SiO_{3/2}]_3$ were obtained.

| Analytical data: | % of C | % of H | % of N | % of Si |
|---|---|---|---|---|
| Theory: | 36.46 | 6.12 | 4.72 | 28.42 |
| Found: | 34.89 | 5.95 | 4.78 | 27.26 |

EXAMPLE 17

10 g of the polymeric amine having units of the formula $N[CH_2CH_2CH_2SiO_{3/2}]_3$, prepared according to Example 16, were stirred for 2 hours in a beaker in 100 ml of a 1N HCl solution. The solids were then filtered off and washed with $H_2O$, and the filtrate which had been combined with the washings was titrated to the neutral endpoint with 1N NaOH solution. This titration showed that 33% of the amount of HCl originally present had disappeared. This corresponds to a 96.7% utilization of basic nitrogen present in the polymeric solid.

EXAMPLE 18

10 g of the polymeric amine obtained according to Example 15 were dealt with in a manner analogous to Example 17. The result was that after stirring for 2 hours 93.8% of the nitrogen present was utilized.

We claim:

1. A polymeric tertiary or secondary organosiloxane amine with a silica-type backbone, comprised of units of the formula:

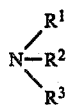 (1)

in which $R^1$ and $R^2$ represent a group of the formula

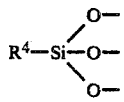 (2)

$R^4$ is alkylene having 3 to 10 C atoms or cycloalkylene having 5 to 8 C atoms or represents the units

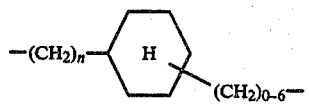

or

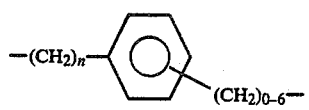

in which n indicates 1 to 6 methylene, $R^1$ and $R^2$ can be identical or different and the free valencies of the oxygen atoms are saturated either by silicon atoms of further groups of the formula (2) and/or by crosslinking bridge members

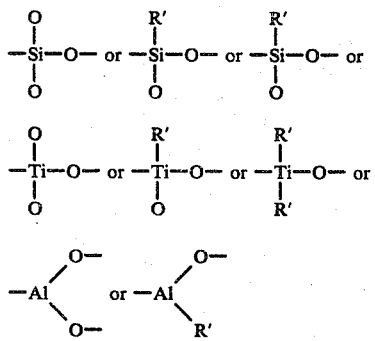

in which R' is methyl or ethyl and in which the ratio of the silicon atoms in (2) to the bridge atoms silicon, titanium and aluminum is 1:0 to 1:10, $R^3$ has the same general meaning as $R^1$ and $R^2$ or represents hydrogen, a linear or branched alkyl having 1 to 10 C atoms or cycloalkyl having 5 to 8 C atoms or benzyl.

2. A polymeric tertiary or secondary organosiloxane amine as claimed in claim 1, wherein $R^4$ is linear or branched alkylene.

3. A polymeric tertiary or secondary organosiloxane amine as claimed in claim 1 or 2, wherein $R^1$, $R^2$ and $R^3$ are identical to one another.

4. A polymeric amine as claimed in claims 1 or 2, comprised of units $N(CH_2-CH_2-CH_2SiO_{3/2})_3$ 5. A process for preparing the polymeric tertiary organosiloxane amine as claimed in claims 1 or 2, comprising reacting a primary amine having a substituent comprised of:

an alkyl group having 1 to 10 C atoms,
a cycloalkyl group having 5 to 8 C atoms,
a benzyl group,
an alkylene group having 3 to 10 C atoms or a cycloalkylene grouping having 5 to 8 C atoms, said alkylene group being bonded to a trialkoxysilyl group wherein the alkoxy contains 1 to 5 C atoms,
or of a group

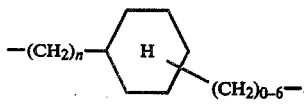

or

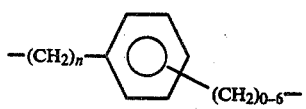

in which n indicates 1 to 6 methylene groups, with a halogenoorganotrialkoxysilane wherein the alkoxy contains 1 to 5 C atoms and in which the organic group is alkylene having 3 to 10 C atoms, cycloalkylene having 5 to 8 C atoms or

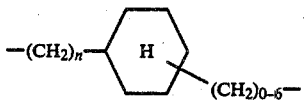

or

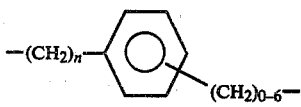

in which n indicates 1 to 6 halogen-terminated methylene, in the course of 5 to 48 hours to form a quanternary salt, deprotonating the resulting quaternary salts by means of at least stoichiometric amounts of an organic or inorganic base, distilling to recover the amine components formed and reacting the component which predominantly contains tertiary amine with at least the amount of water required for complete hydrolysis and condensation and drying.

6. The process as defined in claim 5, which further comprises heat-treating at about 200°–350° C.

7. A process for preparing the polymeric tertiary organosiloxane amine as claimed in claims 1 or 2 comprising reacting a secondary bis-(trialkoxysilylorgano)amine in which the organic group has the meaning of $R^4$ and the alkoxy groups have 1 to 5 C atoms with a halogenoorganotrialkoxysilane in which organic group and alkoxy groups have the same meaning as in the said secondary bis-(trialkoxysilylorgano)amine reactant, or with a linear or branched alkyl halide having 1 to 10 C atoms, a cycloalkyl halide having 5 to 8 C atoms or a benzyl halide, deprotonating the resulting quaternary salt with at least stoichiometric amounts of an organic or inorganic base, and further reacting the tertiary amine with at least the amount of water required for complete hydrolysis and condensation, and drying.

8. A process for preparing the polymeric tertiary organosiloxane amine as claimed in claim 1 or 2, comprising reacting a secondary amine having a trialkoxysilylorgano substituent in which the organic group has the meaning of $R^4$ and the alkoxy groups have 1 to 5 C atoms and a substituent comprised of a linear or branched alkyl group having 1 to 10 C atoms or a cycloalkyl group having 5 to 8 C atoms or a benzyl group with a halogenoorganotrialkoxysilane in which organic group and alkoxy groups have the same meaning as in the case of the trialkoxysilylorgano substituents of the said secondary amine reactant, deprotonating the resulting quaternary salt, with at least stoichiometric amounts of an organic or inorganic base, and further reacting the tertiary amine, with at least the amount of water required for complete hydrolysis and condensation, and drying.

9. The process as claimed in claim 5, wherein the primary amine is reacted with an iodo-, bromo- or chloro-organotrialkoxysilane.

10. The process as claimed in claim 7, wherein the secondary amine is reacted with an iodo-, bromo- or chloro-organotrialkoxysilane.

11. The process as claimed in claim 8, wherein the secondary amine is reacted with an iodo-, bromo- or chloro-organotrialkoxysilane.

12. The process as claimed in claim 5, wherein the alkyl group and/or trialkoxysilylalkyl group on the amine nitrogen and the alkyl group in the halogenoalkyltrialkoxysilane are linear or branched.

13. The process as claimed in claim 5, wherein the reaction of the amine with the halogenoorganotrialkoxysilane is carried out at a temperature between room temperature and 300° C.

14. The process as claimed in claim 13, wherein the reaction is carried out at an elevated pressure which corresponds to the sum of the partial pressures of the components of the reaction mixture at the reaction temperature used.

15. The process as claimed in claim 5, wherein sodium methylate, potassium methylate, sodium ethylate, potassium ethylate, sodium propylate, potassium propylate, sodium butylate, potassium butylate, sodium pentylate, potassium pentylate, alkali metal hydroxide, alkaline earth metal hydroxide, alkali metal bicarbonate, alkali metal carbonate or ammonia are used for the deprotonation.

16. The process as claimed in claim 15, wherein the deprotonation is carried out in an organic solvent.

17. The process as claimed in claim 5, wherein the hydrolysis and condensation are carried out at room temperature to reflux temperature of the reaction mixture.

18. The process as claimed in claim 5, wherein drying is carried out at room temperature to 250° C., if desired in vacuo.

19. The process as claimed in claim 6, wherein the heat treating is carried out for at least one hour up to four days.

20. A process for preparing the secondary polymeric amine as claimed in claim 1 or 2, comprising reacting a bis-(trialkoxysilanorgano)-amine in which the organic group has the meaning of $R^4$ and the alkoxy groups have 1 to 5 C atoms, with at least the amount of water required for complete hydrolysis and condensation and drying.

21. The process of claim 20, wherein the dried solid is heated at about 200°–350° C.

22. The process as claimed in claim 20, wherein the trialkoxysilylalkyl groups on the amine nitrogen are linear or branched.

23. The process as claimed in claim 20, wherein the hydrolysis and condensation are caried out at room temperature to the reflux temperature of the reaction mixture.

24. The process as claimed in claim 20, wherein drying is carried out at room temperature to 250° C., if desired in vacuo.

25. The process as claimed in claim 20, wherein a heat treatment is carried out for at least one hour up to four days.

26. A process for preparing the polymeric tertiary organosiloxane amine as claimed in claim 1 or 2, wherein $R^1$, $R^2$ and $R^3$ are identical comprising reacting ammonia with a halogenoorganotrialkoxysilane in which the organic group is alkylene having 3 to 10 carbons, or cycloalkylene of 5 to 8 carbons, or

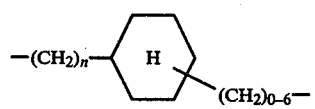

or

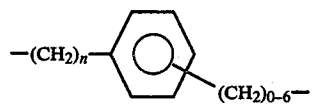

wherein n is 1 to 6,
and the alkoxy groups have 1 to 5 C atoms, at a temperature from below room temperature to 250° C. and under a pressure which corresponds to the sum of the partial pressures of the components of the reaction mixture at the reaction temperature used, 1–20 moles of ammonia being employed per 1 mole of halogenoorganotrialkoxysilane, substantially removing excess ammonia, separating off the resulting inorganic salt, removing by distillation ammonia residues as well as small amounts of primary and secondary amines which have been formed and further reacting the remaining tertiary amine, with at least the amount of water required for complete hydrolysis and condensation and drying.

27. The process as claimed in claim 26, wherein ammonia is reacted with an iodo-, bromo- or chloro-organotrialkoxysilane.

28. The process as claimed in claim 26, wherein the alkyl in the halogenoalkyltrialkoxysilane is linear or branched.

29. The process of claim 5 which further comprises reacting the primary amine with the said silane in the presence of a solubilizer.

30. The process of claim 29 which further comprises deprotonating in a solubilizer.

31. The process of claim 30 which further comprises, after deprotonating, separating an inorganic salt from the liquid phase.

32. The process of claim 5 which further comprises reacting said amine component with water after adding at least one of a solubilizer or crosslinking agent of the general formula:

$$Me(OR)_{2-4}R'_{0-2}$$

or $$Al(OR)_{2-3}R'_{0-1}$$

which Me is Si, or Ti, R is alkyl of 1 to 5 carbons, and R' is methyl or ethyl.

33. The process of claim 7 which further comprises deprotonating the quaternary salt in a solubilizer.

34. The process of claim 33 which further comprises separating the resulting inorganic salt from the liquid phase.

35. The process of claim 7 which further comprises reacting said tertiary amine with water after adding at least one of a solubilizer or a crosslinking agent of the formula:

$$Me(OR)_{2-4}R'_{0-2}$$

or $$Al(OR)_{2-3}R'_{0-1}$$

wherein Me is Si or Ti, R is alkyl of 1 to 5 carbons and R' is methyl or ethyl.

36. The process of claim 7 wherein the product is heat treated at about 200°–350° C.

37. The process of claim 8 which further comprises deprotonating in the presence of a solubilizer.

38. The process of claim 8 which further comprises separating the resulting inorganic salt from the liquid phase after deprotonating.

39. The process of claim 8 which further comprises reacting said tertiary amine with water after adding at least one of a solubilizer or a crosslinking agent of the formula:

$$Me(OR)_{2-4}R'_{0-2}$$

or $$Al(OR)_{2-3}R'_{0-1}$$

wherein Me is Si or Ti, R is alkyl of 1 to 5 carbons and R' is methyl or ethyl.

40. The process of claim 8 which further comprises heating the product at 200°–350° C.

41. The process of claim 16 wherein the solvent is an alcohol which corresponds to the alkoxyl groups bonded to the silicon atoms of one or both reactants.

42. The process of claim 20 which further comprises adding a solubilizer.

43. A process for preparing a polymeric tertiary organosiloxane amine comprised of units of the formula:

$$N(CH_2CH_2CH_2SiO_{3/2})_3$$

comprising reacting ammonia with a halogenoorganotrialkoxysilane in which the organic group is alkylene having 3 carbons, and the alkoxy groups have 1 to 5 C atoms, at temperature from below room temperature to 250° C. and under a pressure which corresponds to the sum of the partial pressures of the components of the reaction mixture at the reaction temperature used, 1–20 moles of ammonia being employed per 1 mole of halogenoorganotrialkoxysilane, substantially removing excess ammonia, separating off the resulting inorganic salt, removing by distillation ammonia residues as well as small amounts of primary and secondary amines which have been formed and further heating the remaining tertiary amine, with at least the amount of water required for complete hydrolysis and condensation and drying.

44. The process of claim 26 wherein the reaction of ammonia with said alkoxysilane takes place in the presence of a solubilizer.

45. The process of claim 26 which further comprises adding at least one of a solubilizer or crosslinking agent of the formula:

$$Me(OR)_{2-4}R'_{0-2}$$

or $$Al(OR)_{2-3}R'_{0-1}$$

wherein Me is Si or Ti, R is alkyl containing 1 to 5 carbons, and R' is methyl or ethyl.

46. The process of claim 26 where the product is heated at 200°–350° C.

47. The process of claim 43 where the reaction of ammonia with said alkoxysilane takes place in the presence of a solubilizer.

48. The process of claim 43 which further comprises adding at least one of a solubilizer or crosslinking agent of the formula:

$$Me(OR)_{2-4}R'_{0-2}$$

or $$Al(OR)_{2-3}R'_{0-1}$$

wherein Me is Si or Ti, R is alkyl containing 1 to 5 carbons, and R' is methyl or ethyl.

49. The process of claim 43 where the product is heated at 200°–350° C.

* * * * *